United States Patent
Kang et al.

(10) Patent No.: US 10,765,715 B2
(45) Date of Patent: Sep. 8, 2020

(54) **COMPOSITION CONTAINING SAPONINS OF *PANAX GINSENG* AS ACTIVE INGREDIENT**

(71) Applicant: KYUNGSUNG UNIVERSITY INDUSTRY COOPERATION FOUNDATION, Busan (KR)

(72) Inventors: Jae Seon Kang, Busan (KR); Bo Suel Kim, Busan (KR); Heyong-Soo Kim, Busan (KR); Gyu-Jin Rho, Jinju-si (KR); Sin-Ja Bae, Busan (KR); Seo Hyun Lee, Busan (KR); Jong Jin Park, Busan (KR); Choel-Min Kim, Busan (KR)

(73) Assignee: KOREAN DRUG CO., LTD., Icheon-si, Gyeonggi-do (KR)

( * ) Notice: Subject to any disclaimer, the term of this patent is extended or adjusted under 35 U.S.C. 154(b) by 122 days.

(21) Appl. No.: 16/062,101

(22) PCT Filed: Oct. 28, 2016

(86) PCT No.: PCT/KR2016/012231
§ 371 (c)(1),
(2) Date: Jun. 13, 2018

(87) PCT Pub. No.: WO2017/104966
PCT Pub. Date: Jun. 22, 2017

(65) Prior Publication Data
US 2018/0369309 A1    Dec. 27, 2018

(30) Foreign Application Priority Data
Dec. 14, 2015 (KR) .................. 10-2015-0178493

(51) Int. Cl.
*C07J 1/00* (2006.01)
*A61K 36/258* (2006.01)
(Continued)

(52) U.S. Cl.
CPC ............ *A61K 36/258* (2013.01); *A23L 33/10* (2016.08); *A23L 33/105* (2016.08);
(Continued)

(58) Field of Classification Search
CPC ................................... C07J 1/00; C07H 7/04
See application file for complete search history.

(56) References Cited

FOREIGN PATENT DOCUMENTS

KR       10-0881634 B1      2/2009
KR    10-2015-0101667 A     9/2015
(Continued)

OTHER PUBLICATIONS

Korea Polytechnic University Industry Academic Cooperation Foundation (KR 1020120089974 A), KIPO English machine translation, 2012.*

(Continued)

*Primary Examiner* — Rosanne Kosson
(74) *Attorney, Agent, or Firm* — Revolution IP, PLLC

(57) ABSTRACT

Disclosed are uses of ginseng saponin, which contains at least 90% of a compound K, Rd, F2, and Rg3 as a main ingredient and has effects in extending the lifespan of the cell, promoting the cell differentiation, increasing the number of red blood cells, and reducing the triglycerides by extracting, heat-treating, and enzyme-converting the ginseng saponin to prepare active saponins Rd, F2, and Rg3 including a compound K.

7 Claims, 10 Drawing Sheets

(51) Int. Cl.
  *A23L 33/105* (2016.01)
  *A23L 33/10* (2016.01)
  *A61K 31/575* (2006.01)
  *A61K 31/704* (2006.01)

(52) U.S. Cl.
  CPC .......... *A61K 31/575* (2013.01); *A61K 31/704* (2013.01); *A61K 2236/15* (2013.01); *A61K 2236/333* (2013.01); *A61K 2236/51* (2013.01); *A61K 2236/53* (2013.01)

(56) References Cited

FOREIGN PATENT DOCUMENTS

KR 10-1574558 B1 12/2015
KR 10-2016-0072802 A 6/2016

OTHER PUBLICATIONS

International Search Report for PCT/KR2016/012231 dated May 8, 2017 from Korean Intellectual Property Office.

Lee, H.-J. et al., "The effect of ginsenosides on hepatogenic differentiation using placenta-derived stem cells as an in vitro screening system", Molecular and Cellular Toxicology, 2013, No. 9. 185-193.

Li, J. et al., "Ginsenoside-Rd, a purified component from panax notoginseng saponins, prevents atherosclerosis in apoE knockout mice", European Journal of Pharmacology, 2011, vol. 652, pp. 104-110.

Li. G. -X. et al., "The protective effects of ginsenosides on human erythrocytes against hemin-induced hemolysis", Food and Chemical Toxicology, 2008, vol. 46, pp. 886-892.

Hai-Dan Yuan et al., "Pectinase-Processed Ginseng Radix (GINST) Ameliorates Hyperglycemia and Hyperlipidemia in High Fat Diet-Fed ICR Mice", Biomolecules & Therapeutics, 2012, vol. 20(2), pp. 220-225.

* cited by examiner

FIG. 7

| Indicator | RBC X10^3 | WBC X10^3 | Hct | Hb g/dl | Platalet X10^3 | TG | Etc. (T-cho,HDL,LDL) |
|---|---|---|---|---|---|---|---|
| Normal | 7 | 5~9 | 45% | 10~20 | −1.000 | 450 | Nor |
| Test | 9.12 | 6.65 | 57.8% | 16.9 | 1160 | 250 | Nor |

COMPOSITION CONTAINING SAPONINS OF *PANAX GINSENG* AS ACTIVE INGREDIENT

BACKGROUND OF THE INVENTION

The present invention relates to uses of ginseng saponin such as wild ginseng, wood-cultivated ginseng, cultivated roots, water culture ginseng, *Panax quinquefolius* L., *Panax notoginseng*, or red ginseng, and the like, and more particularly, to ginseng saponin (hereinafter, referred to as 'CKS'), which contains at least 90% of a compound K, Rd, F2, and Rg3 as a main ingredient and has effects in extending the lifespan of the cell, promoting the cell differentiation, increasing the number of red blood cells, and reducing the triglycerides by extracting, heat-treating, and enzyme-converting the ginseng saponin to prepare active saponins Rd, F2, and Rg3 including the compound K.

Saponin and non-saponin substances (panacen, polysaccharides, amino acid derivatives, polyacetylene derivatives, and phenol compounds), which are contained in ginsengs, have excellent pharmacological activity and excellent efficacy in elimination of harmful free radicals, and have excellent efficacy in anticancer, blood pressure drop, liquid lowering, and hepatotoxicity. *Ginseng* saponin, which is well known as a main pharmacological component of the ginsengs, is divided into protopanaxadiol (PPD)-based saponin and protopanaxatriol (PPT)-based saponin. The PPD-based saponin has a structure in which various substituents are bonded to the PPD, which is a basic structure, and ginsenosides Rb1, Rb2, Rc, Rd, F2, and Rg3 and a compound K are representative saponins. The PPT-based saponin is a basic structure of PPT, and ginsenosides Re, Rf, Rg1, Rh1, and are representative.

In general, many glycoside compounds present in the natural world tend to have increased physiological activity when the sugar is degraded and become an aglycon rather than the glycoside compounds themselves. In the case of ginseng saponin, it is known that ginsenosides Rg3, Rh1, Rh2, F2, CY, and CK produced by hydrolysis of some of sugars have better effects in terms of absorption into the living body and physiological activity than ginsenosides Rb1, Rb2, Rd, and Re bonded with three or more sugars. It is known that ginseng saponin, which is bonded with many sugars, is absorbed into the body in the small intestine in a very small amount. As a result of an experiment on the hydrolysis ability of ginsenoside Rb1 from intestinal microorganisms extracted from human excreta, it is showed that 21% of the intestinal microorganisms have no decomposition ability. It was confirmed that 70% of the intestinal microorganisms having decomposition ability had a great difference in ability of decomposing the ginseng saponin.

In general, ginseng products including saponin components are composed of ginseng saponins consisting of ingredient having high solubility in water. It is known that the components in an inactive state have high solubility in water, but are not easily absorbed in the intestines and thus there is little effect. However, when the ingredients are activated and changed to an active ingredient, the ingredients are not easily dissolved in water, but the absorbability in the body is increased, and thus, the effect is exerted well.

In the present invention, the term "the active type" used in the active saponin, the active wood-cultivated ginseng, the active ingredient, and the like means a characteristic of saponin or ginsenoside of the ginseng processed by the present invention. The sugars attached to a nucleus of saponin are separated, and as a result, the total content of saponin is higher than that of ordinary wild ginseng, wood-cultivated ginseng or ginseng and absorbed in human body to exert its effect. That is, the active type means saponin which has a better effect in terms of adsorption in the human body or physiological activity as one or at least two ginsenosides selected from the group consisting of ginsenosides Rg3, Rh1, Rh2, F2, CY, and CK produced by hydrolysis of some of sugars, instead of ginsenosides Rb1, Rb2, Rd, and Re bonded with three or more sugars.

As described above, the active ingredient is an ingredient in which the sugar attached to ginseng saponin is separated from the sugar and absorbed in the human body to exert its effect. This process is mainly a process of decomposition by heat or decomposition by enzymes, and some of the active ingredients are activated by the intestinal microorganisms and then absorbed. Particularly, it is known that it is very difficult to manufacture a compound K, which is an active ingredient.

The present inventors tried to find a use for anti-aging by preparing and studying the CKS. Aging is a state in which a living body is unable to perform its normal functions due to functional deterioration of cells and organs constituting the living body, the homeostasis deterioration of the living body due to excessive accumulation of waste products, and induction of cell suicide. The aging can also be defined as a process in which the susceptibility to disease and death increases and the living body becomes debilitated. However, these causes are diverse and complicated, and it is difficult to define the cause to one cause.

The present invention aims to identify internal factors among various causes of aging through blood analysis. With age, deterioration of a liver function, deterioration of a kidney function, memory loss, and especially, excessive increase in total fat and triglyceride levels cause problems in the blood vessels and cause many diseases. Therefore, the results are observed through blood analysis.

As a result, Sprague Dawley rats (hereinafter, referred to as SD rats) with 12 months old were purchased and bred for 19 months and then intraperitoneally administered with CKS for 37 days from 20 months of age, and compared with a non-administered control group. It is very difficult to manufacture a compound K and therefore, it is not easily to purchase and experiment the compound K due to a disadvantage of high cost. The present inventors have developed a technique for producing a large amount of compound K by enzyme conversion over a long period of time, and administered CKS containing the prepared compound K to an aged Sprague Dawley Rat (hereinafter, referred to as a SD Rat), and performed Blood analysis. As a result of blood analysis, the decrease of triglycerides was obviously shown, and there was an increase of red blood cells. In contrast to the control group with much decreased activity, the drug-administered group was active. The present inventors tried to find an additional reason in addition to the results of the increase in motility (Korean Patent Application No. 10-2014-0023244) filed by the present inventors and additionally confirmed an effect of CKS through the blood analysis. The US Food and Drug Administration (FDA) has approved an indication for ruxolitinib, a therapeutic agent for bone marrow fibrosis, to be prescribed to patients with polycythemia vera. Similarly, the CKS can be prescribed to the patients for an effect of increasing red blood cells.

Since it takes a considerable time to secure an aging rodent, there is a difficulty in breeding for a long period of time, and it is quite difficult to design a proper experiment because it is not known when a biofunction is deteriorated. As a result, the present inventors observed the white paper daily rats for up to 19 months, intend to draw the results from fat analysis and hematology analysis using the CKS in the experiment, and intend to draw good results for anti-aging by an experiment on the aging rodent.

In addition, the present inventors found the differentiation effect on stem cells and found the effect on lifespan extension of the cells through cell culture. The differentiation of stem cells means that as many cells as possible can be made in a short time. In particular, reducing the differentiation time means that the number of cells can be increased quickly.

Scholars have studied substances that have an effect of extending a cell lifespan and have made an effort to find a safe substance that inhibits β-galactosidase. However, it is not easy to find such a substance, and it is very difficult to use a substance with secured safety and stability. In particular, the cost should be considered in terms of economy. The CKS, which has been studied for a long time by the present inventors, is considered to be an optimal material in terms of stability, safety, price, and the like. In terms of cell culture, suppression of β-galactosidase in cultured cells means that extension of the lifespan of cells is caused. Scientists have studied substances having an effect of extending the lifespan of cells, and the present inventors have derived a result using CKS having an effect of suppressing the β-galactosidase.

SUMMARY OF THE INVENTION

The present invention has been made in an effort to solve the conventional problems as described above and has the following objects.

An object of the present invention is to provide a composition which is useful for increasing the number of red blood cells and reducing triglycerides by preparing ginseng saponin as an active ingredient by removing attached sugars and containing the ginseng saponin as an active ingredient.

Another object of the present invention is to provide a composition which contains ginseng saponin as an active ingredient and is useful for reducing a differentiation time of stem cells and extending the lifespan of cells by suppressing β-galactosidase in the cell.

Yet another object of the present invention is to provide a composition which contains ginseng saponin as an active ingredient to overcome the problems of persistence of a harmful organic solvent by preparing the ginseng saponin as an active ingredient by using ethyl alcohol in addition to heat treatment and enzyme treatment.

In order to achieve the above objects, the present invention is implemented by the following technical solutions.

An exemplary embodiment of the present invention provides a composition containing ginseng saponin as an active ingredient which is useful for increasing the number of red blood cells, reducing triglycerides, promoting differentiation of stem cells, and extending the lifespan of cells. Specifically, the ginseng saponin is prepared by exposing the ginseng to steam under a pressure of 1.1 kg/cm$^2$ while removing a large amount of moisture at 121° C. for 10 minutes using an automatic temperature and humidity control device with a porous shelf (step S1); continuously injecting air into the ginseng subjected to the step S1 and cooling the ginseng to 90° C. or lower (step S2); repeating further the steps S1 and S2 two times (step S3); cooling the ginseng to room temperature in an automatic temperature control device and pulverizing the ginseng to a particle size of 1 mm or less, after step S3 (step S4); extracting saponin by adding 80% ethyl alcohol to the ginseng subjected to the step S4, and concentrating the extracted saponin (step S5); preparing a suspension by dissolving the concentrated saponin in ethanol and adding sterilized water, after step S5 (step S6): adding and reacting the suspension to a pectinase enzyme solution by one drop, after step S6 (step S7); and precipitating the solution subjected to the reaction of step S7 by centrifugation and concentrating a filtrate by dissolving the generated precipitate in ethyl alcohol, suspending the dissolved precipitate in sterilized physiological saline again and then filtrating the suspended precipitate.

Further, another exemplary embodiment of the present invention provides a pharmaceutical composition which is useful for increasing the number of red blood cells, reducing triglycerides, promoting differentiation of stem cells, and extending the lifespan of cells, in which the ginseng saponin contains 90% or higher of protopanaxadiol-based saponin and the protopanaxadiol-based saponin includes a compound K, Rd, F2, and Rg3 which are active protopanaxadiols.

The present invention has the following effects by the configuration above.

According to the present invention, it is possible to provide a pharmaceutical composition which contains ginseng saponin as an active ingredient by preparing the ginseng saponin as an active ingredient by removing attached sugars and is useful for increasing the number of red blood cells and reducing triglycerides. Further. It is possible to provide a pharmaceutical composition which contains ginseng saponin as an active ingredient which overcomes the problem on persistence of harmful organic solvents to be useful for increasing the number of red blood cells, reducing triglycerides, differentiating the stem cells, and extending the lifespan of the cell.

BRIEF DESCRIPTION OF THE DRAWINGS

FIG. 7 shows results of the blood and blood cells which are analyzed after extracting the blood by administering CKS to the abdominal cavity of 4 SD rats per group once a day for 20 months to 37 days (triglyceride (TG) shows a statistically significant result, a CKS-administered experimental group is reduced by about 55% as 250 mg/dl as compared with a control group showing average 450 mg/dl, and total hematocrit (Hct) is increased from 45% to 57.8%, a level of red blood cells (RBCs) is increased by about 30% from 7×106/μl to 9.12×106 μl).

DETAILED DESCRIPTION OF THE INVENTION

The Applicant will hereinafter describe the technical solutions in detail. The detailed description of known technology, which is considered to be unnecessarily obscured by the gist of the present invention, will be omitted.

Figure 1:
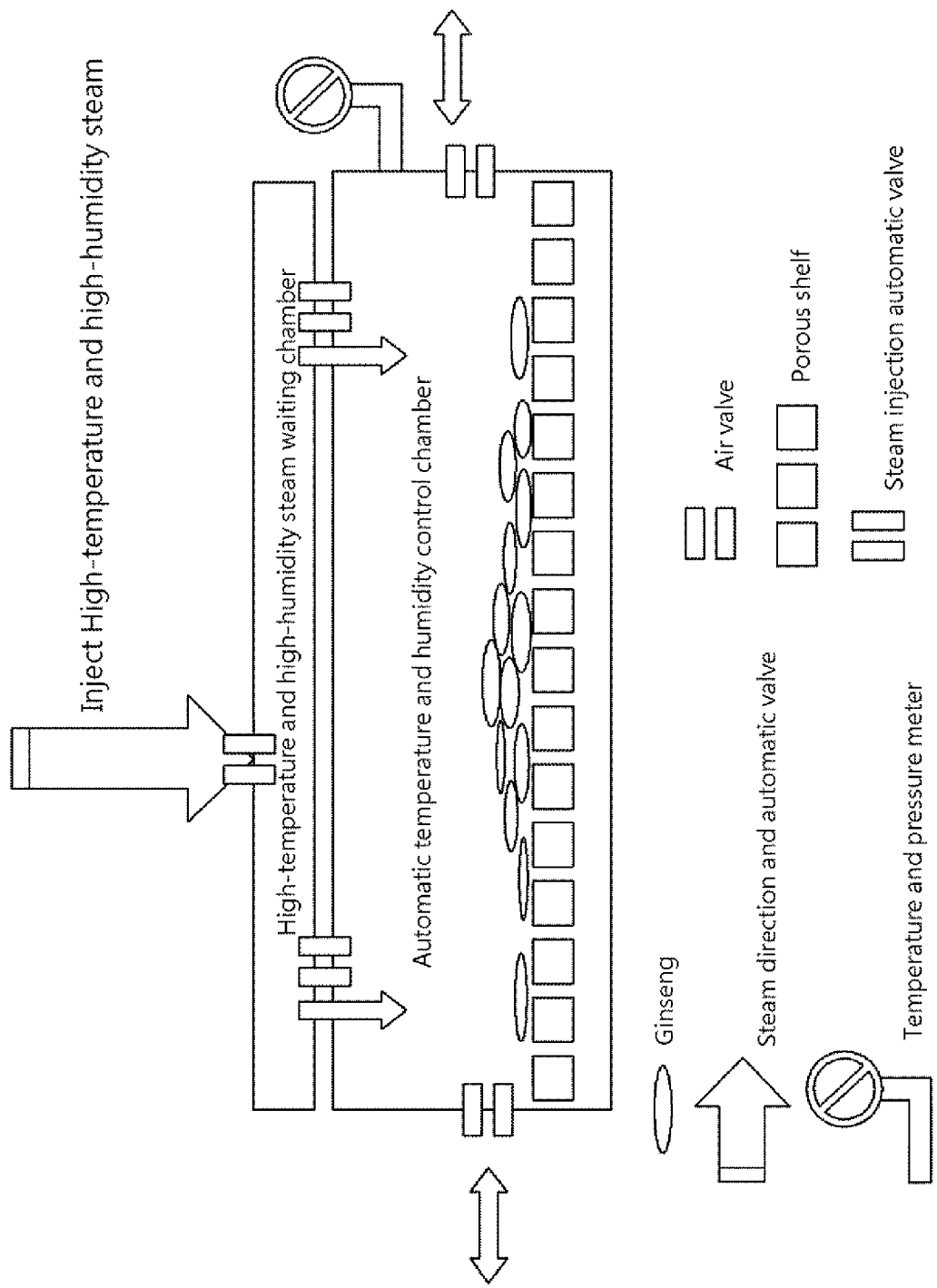
FIG. 1 is a side view of an automatic temperature-humidity control device.
Figure 2:
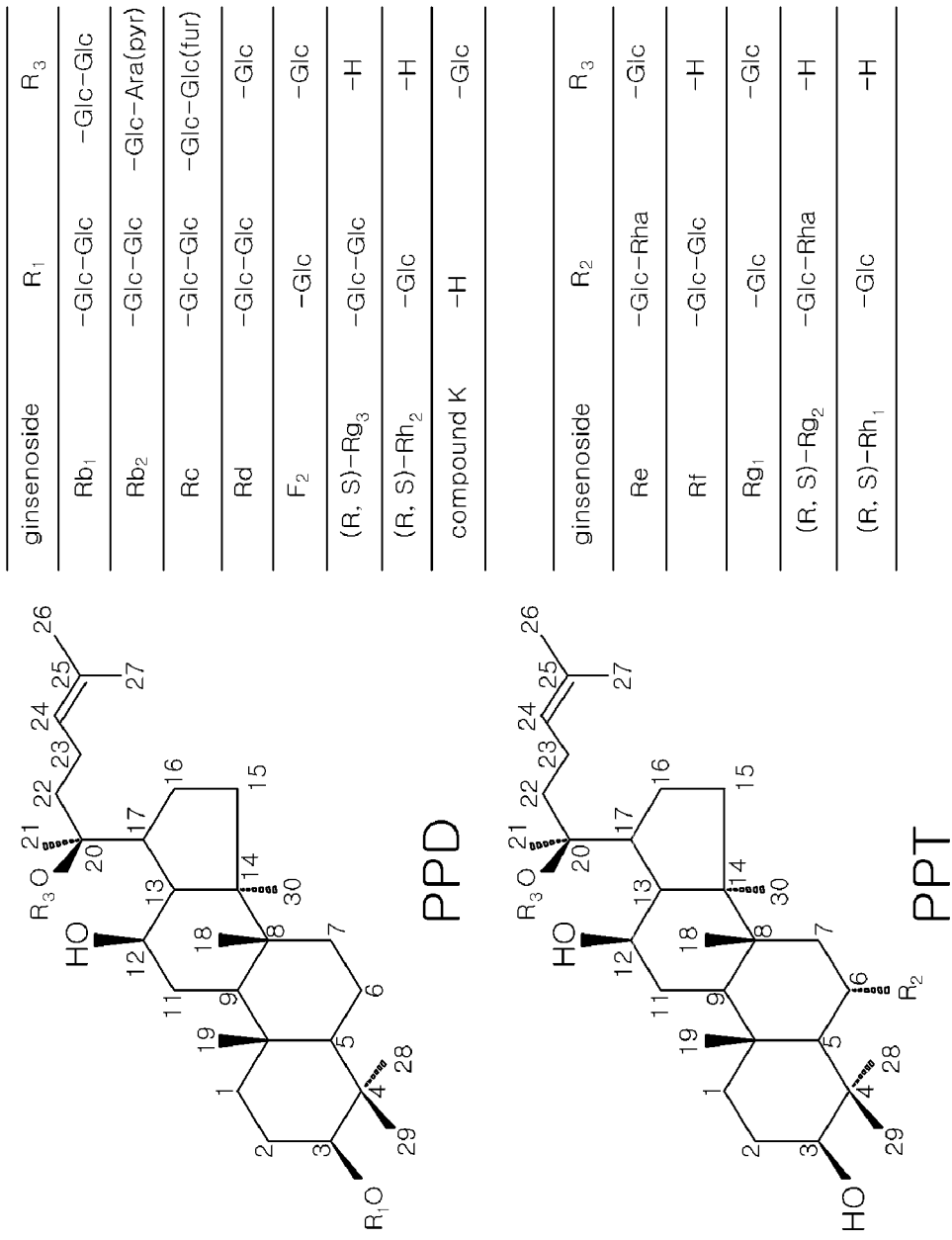
FIG. 2 is a PPT-based saponin structure and a PPD-based saponin structure.
Figure 3:
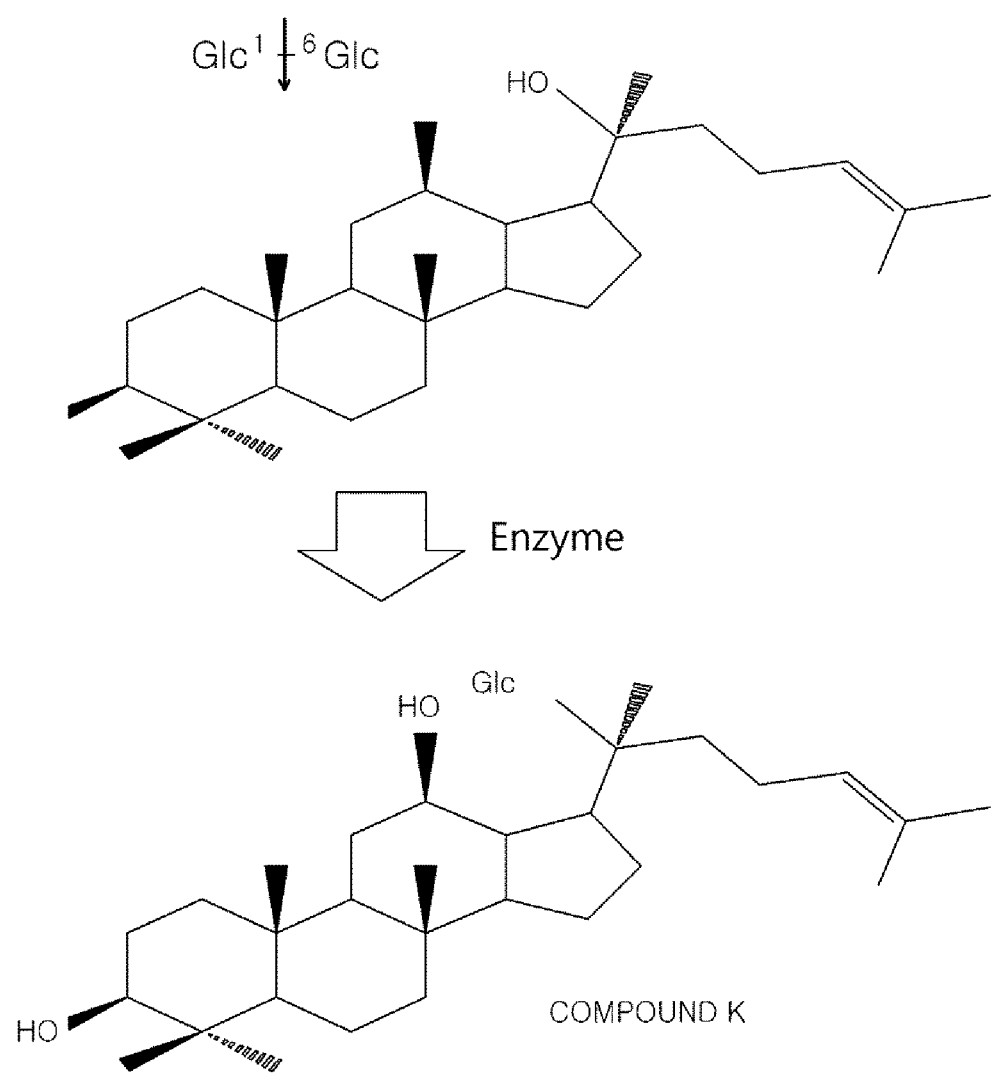
FIG. 3 is a diagram showing a process in which glucose is removed from ginseng saponin by an enzyme reaction (a diagram showing a process of preparing a compound K as active saponin by removing glucose from ginseng saponin Rb1 by an enzyme reaction).

In the present invention, ginseng is heat-treated using an automatic temperature and humidity control device, and the ginseng refers to any one or at least two of roots of wild ginseng, wood-cultivated ginseng, cultivated roots, water culture ginseng, *Panax quinquefolius* L., *Panax notoginseng*, or red ginseng. First, when describing a structure of the automatic temperature and humidity control device through FIG. 1, steam in a high temperature and high pressure steam chamber is sent to an automatic temperature and humidity control chamber through a valve, in which active ginseng is manufactured and dried by continuous operation. When a steam injection automatic valve is opened, an air valve automatically opens, and when the steam is filled in the automatic temperature and humidity control chamber and the air is removed, the air valve closes automatically due to automatic recognition, and when the temperature and the pressure reach activating points, the steam injection automatic valve is closed and maintained for 10 minutes. After 10 minutes, the air valve is automatically opened and the pressure drops. When the temperature reaches 90° C., the air valve closes again and the steam injection valve opens. When the steam is filled in the automatic temperature and humidity control chamber and the air is removed, the air valve automatically closes due to automatic recognition, and when the temperature and the pressure reach activating points, the steam injection automatic valve is closed and maintained for 10 minutes. The above operation is repeated one more time, and the ginseng is heat-treated total three times and activated.

In the present invention, the active ingredient was prepared by heat treatment. Specifically, the heat treatment was performed at 121° C. and 1.1 kg/cm$^2$ for 10 minutes and repeated total three times (prepared as heated saponin, hereinafter referred to as "HS"). The heated saponin was pulverized by a pulverizer and suspended in 80% pharmacopoeia ethanol (alternatively, 80% ethyl alcohol) to extract a saponin ingredient. This is because the extraction of PPD in a 80% ethanol solution is better than PPT. The saponin ingredient extracted above was concentrated by evaporation, which was suspended in water and used as a raw material for PPD active production. The active ingredient was prepared by decomposing the sugar chain of saponin by injecting a suspension material into an enzyme solution by a certain amount using a peristaltic pump (preparation of PPD-based saponin containing compound K, hereinafter referred to as "CKS"). When a reaction material is not added to the enzyme in a certain amount, the yield is low and the reaction does not occur due to an aggregation phenomenon. Accordingly, in the present invention, the PPD-based active ingredient containing the compound k was prepared by injecting the reaction material into the enzyme by a predetermined amount by using a tube peristaltic pump. The prepared active ingredient was collected by centrifugation and then resuspended in ethyl alcohol and filtered to concentrate a filtrate.

Hereinafter, the present invention will be described in detail with reference to Examples and drawings.

Example 1

Ginseng containing wood-cultivated ginseng were placed on a porous shelf for 10 minutes at 121° C. by using an automatic temperature and humidity control device which was filled with steam from which air is removed and exposed to the stream under a pressure of 1.1 kg/cm$^2$ and heat-treated while moisture dropped down to remove a large amount of moisture. The heat-treated ginseng were cooled to 90° C. or lower while the air was injected by opening a ventilation valve and the same operation was further performed two times again.

Example 2

Active ginseng prepared in Example 1 were finely pulverized into particles having a size of 1 mm or less and dried, added with 80% ethyl alcohol, and then sufficiently heated to extract active saponin. Specifically, 60 g of the prepared active ginseng were pulverized and added with 80% ethyl alcohol to extract the active saponin and filtrated by a particle filter of about 500 μm to remove a solid and collect an ethyl alcohol solution (hereinafter, referred to as a 'heat-treated saponin ethanol solution' or 'HS ethanol solution').

The "heat-treated saponin ethanol solution' was concentrated using a rotary evaporator (hereinafter, referred to as 'heat-treated saponin concentrate' or 'HS concentrate'. The 'heat-treated saponin concentrate' was dissolved in a small amount of ethyl alcohol (ethanol) and added with sterilized distilled water to prepare a suspension (hereinafter, referred to as a 'heat-treated saponin suspension', concentration of 0.23 w/v %). The 'heat-treated saponin suspension' was kept at 50° C. or higher in order to prevent the generation of harmful bacteria due to contamination.

Figure 4:
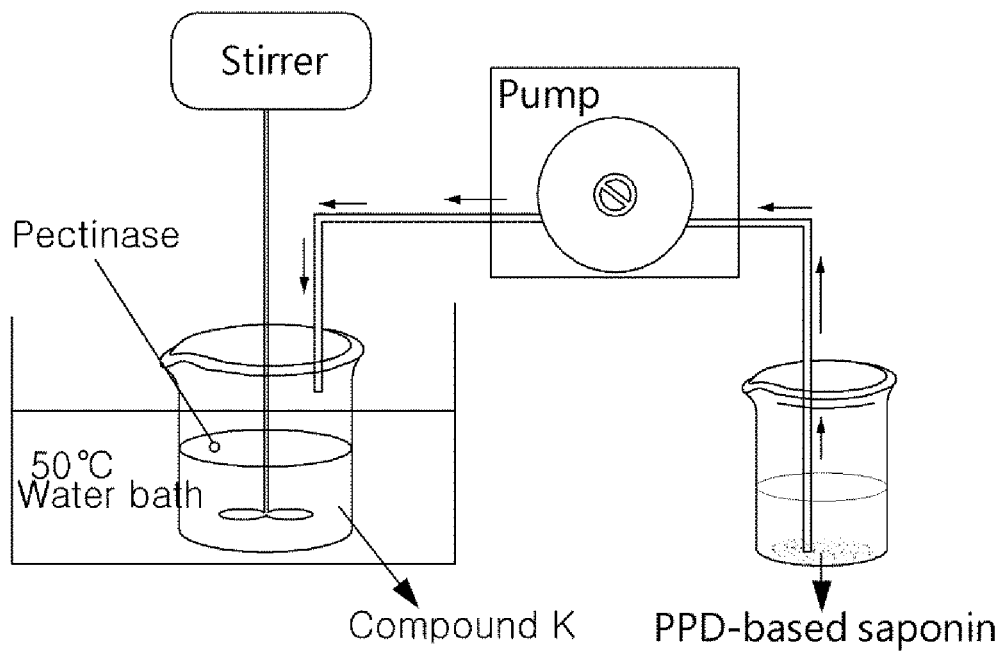
FIG. 4 is a diagram showing a process in which glucose is removed from a 'heat-treated saponin suspension'.
Figure 5:
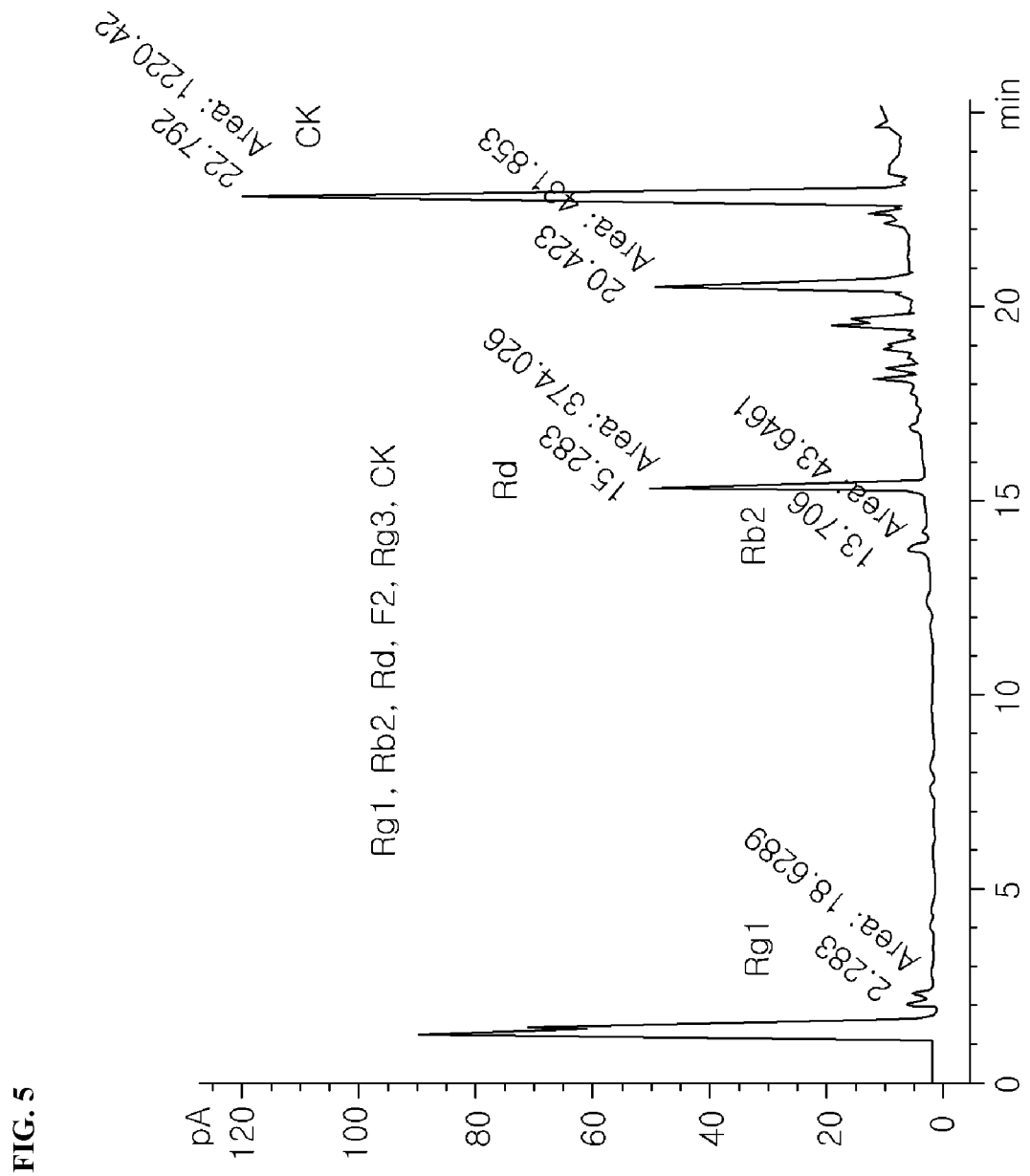
FIG. 5 is an analysis result of active saponin of CKS by HPLC (showing a result of a compound k of 52%, Rd of 34.4%, F2 of 2.69%, and Rg3 of 2% with respect to the total saponin content).
Figure 6:
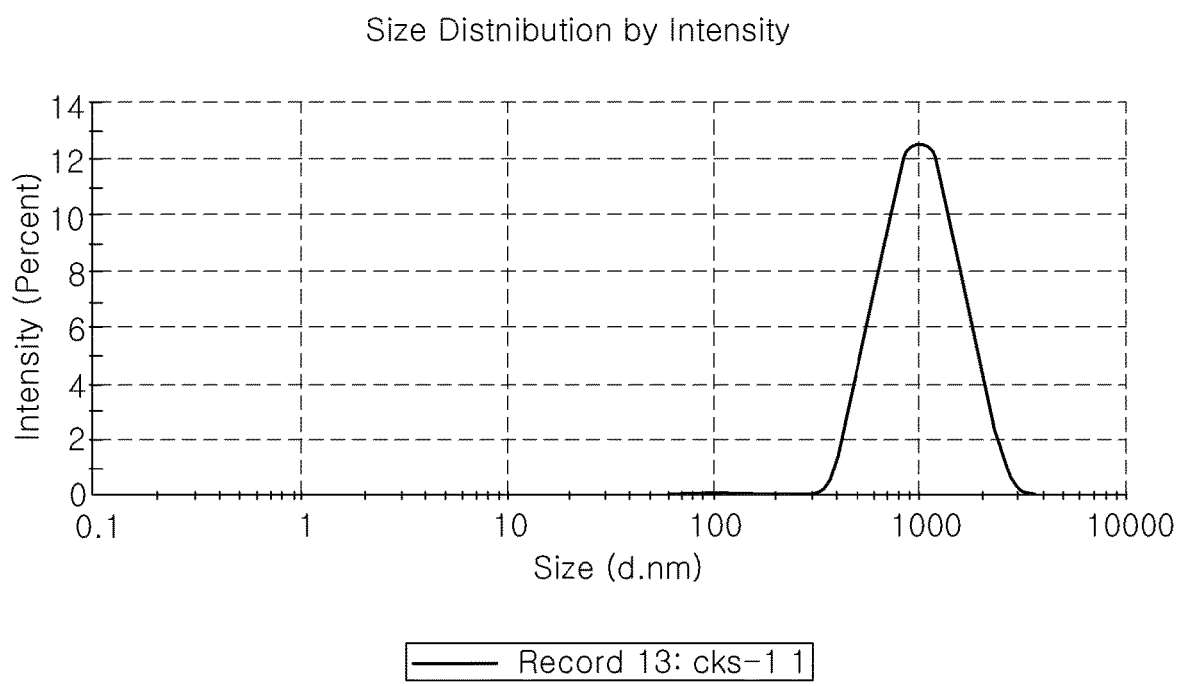
FIG. 6 is an analysis result of a CKS solution by a particle size analyzer (it is analyzed that an average particle size is 1 μm or less).

Separately from the 'heat-treated saponin suspension', an aqueous solution (2.4% pectinase solution) containing pectinase (trademark name of Rapidase, DSM food, Netherlands) was kept at a temperature of 50° C. using an automatic temperature device (hereinafter referred to as an 'enzyme solution'), and the 'heat-treated saponin suspension' was continuously injected to the enzyme solution by one drop. An injection speed of the 'heat-treated saponin suspension' was 50 ml/min. More specifically, as shown in FIG. 4, the 'heat-treated saponin suspension' was injected into the enzyme solution by a predetermined amount (50 ml/min) using a tube peristaltic pump and the prepared ingredients were collected by centrifugation and then suspended with ethyl ethanol again and filtered to concentrate a filtrate to finally secure a concentrate. 1 to 1.4 g of the final concentrate was prepared from 60 g of wood-cultivated ginseng having the moisture content of 30% and among them, the content of a compound k (CK) was highest of 52%, the content of Rd was 34.4%, the contend of F2 was 2.7%, and the content of Rg3 was 2% (see FIGS. 5 and 6).

TABLE 1

| Saponin | compound K | F2 | Rd | Rg3 |
|---|---|---|---|---|
| Content | 52% | 2.69% | 34.4 | 2% |

The final concentrate is hereinafter referred to as CKS because the PPD-based active ingredients such as CK, Rd, F2, and Rg3 occupy 91% or higher and the content of the compound k (CK) is highest as 52%.

Example 3

Preparation and Analysis of CKS Suspension

The prepared CKS was weighted, added and dissolved with ethyl alcohol having 10 times weight, and then mixed and suspended with a sterile physiological saline containing 0.01% polysorbate 80. The suspension prepared above was analyzed using a particle size analyzer (Malvern nano ZS-902). As the analyzed result, the average size of the particles was 785.5 nm and the size was less than 1 μm.

Example 4

Animal Administration Experiment

Male SD rats grown in an animal room for up to 19 months were used for the experiment and were administered for a total of 37 days from 20 months. A total of 10 SD rats were divided into two groups of 5 SD rats. In a control group, 1 ml of sterile physiological saline was administered to the abdominal cavity once per day, and in an experimental group as a CKS-administered group, CKS was administered to the abdominal cavity at a concentration of 1.25 mg/kg once per day and an aseptic CKS suspension was used. One rat in the experimental group that had natural cancer during the experiment was eliminated from the experiment. At day 38, the blood was collected and used for analysis. For the blood analysis, data were obtained by Green Cross Labs Co., Ltd., a specialized blood analysis agency.

As the analyzed result, the red blood cells (RBCs) were increased to 30% and hematocrit (Hct) was increased from 45% to 57.8%. In addition, there was no change in other hemoglobin (Hb), platelet, total cholesterol (T-cho), high-density cholesterol (HDL), and low-density cholesterol (LDL) (see FIG. 7).

Example 5

Figure 8:
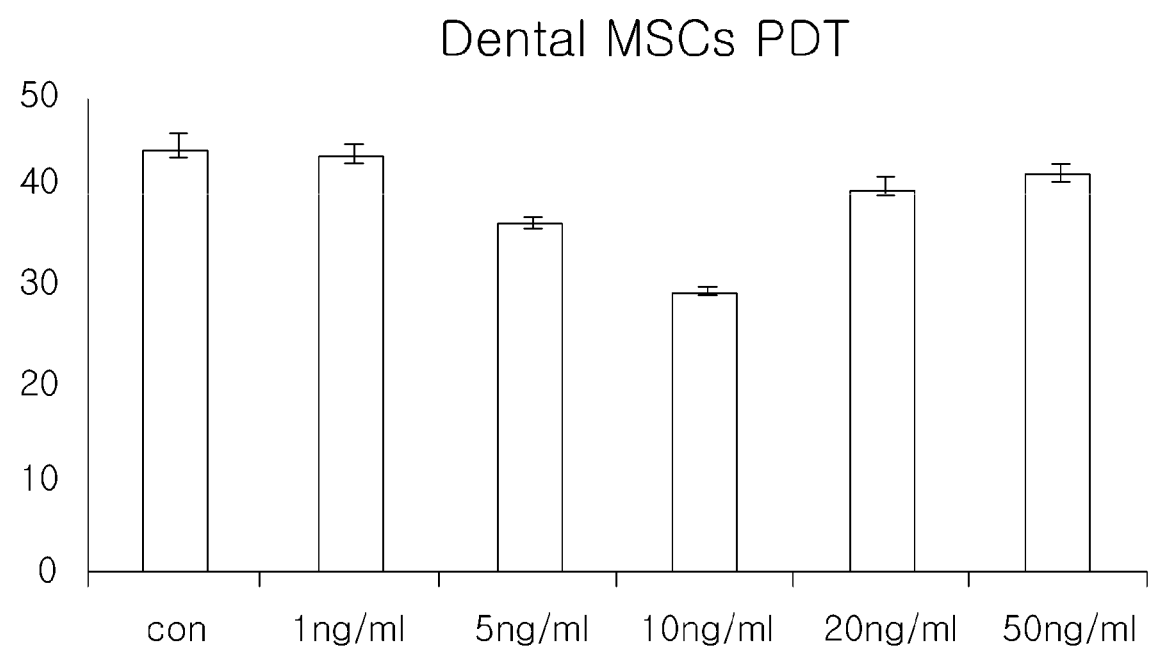
FIG. 8 shows a result of observing a doubling time of mesenchymal stem cells (MSCs) in an experiment using human tooth-derived stem cells (as a result, shows the smallest population stem cell doubling time (PDT) at a concentration of 10 ng/ml).
Figure 9:
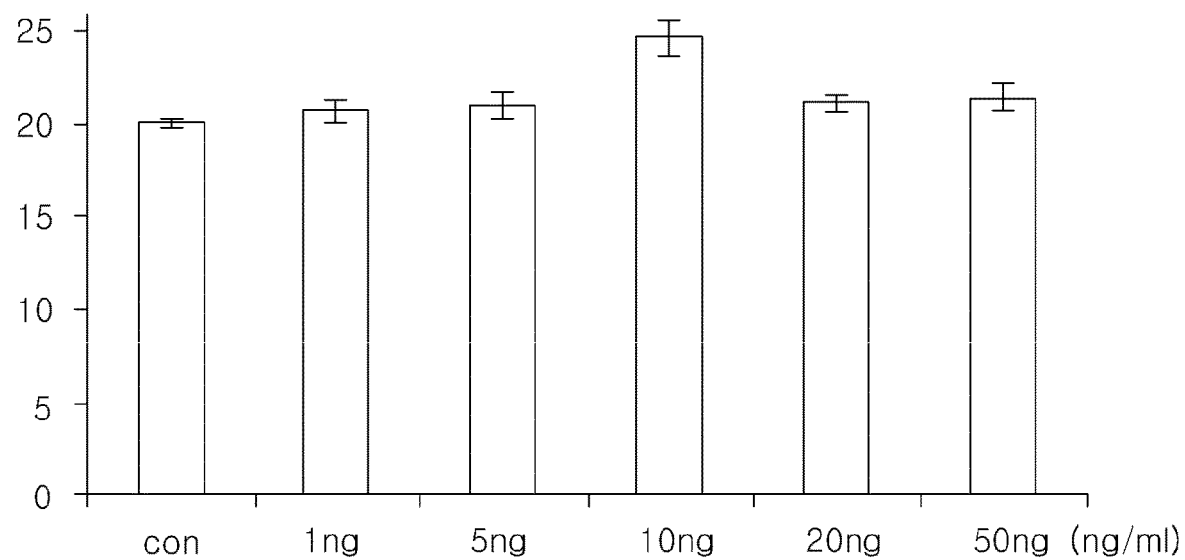
FIG. 9 shows a result of measuring a PDT for human-derived leukocyte cancer cells in an experiment using human tooth-derived stem cells (shows the longest time at a concentration of 10 ng/ml to make a growth speed of the leukocyte cancer cells slow.
Figure 10:
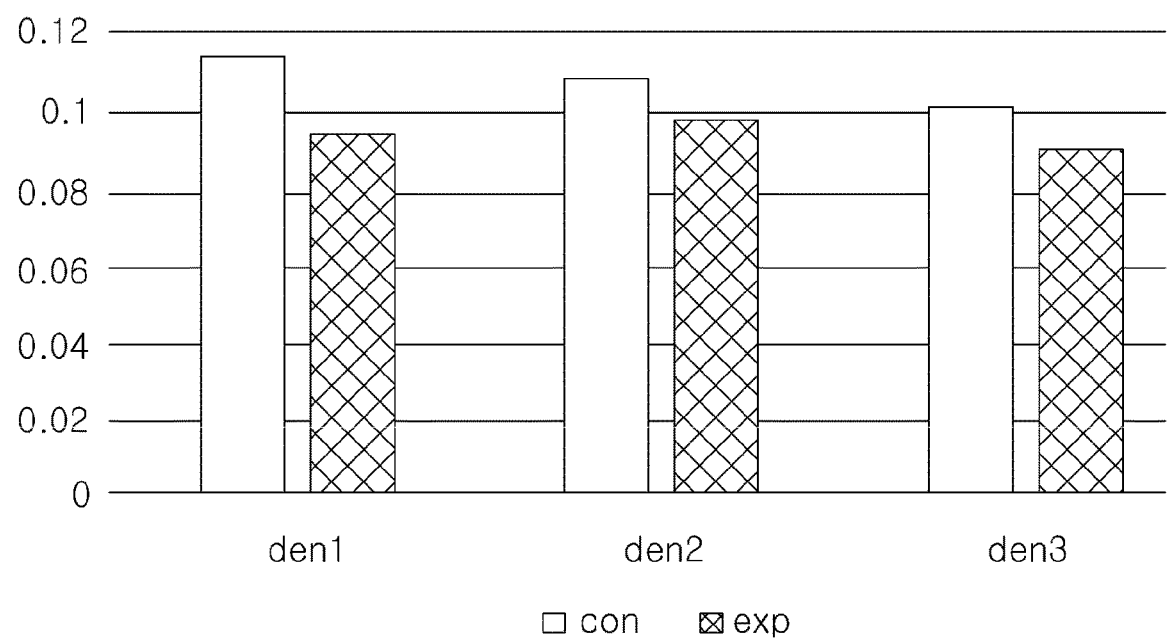
FIG. 10 shows a content of β-galactosidase in cells, which is evaluated using human tooth-derived stem cells.

The human wisdom tooth was pulled to extract stem cells. The number of cells was counted by adding CKS for each concentration while stem cells were cultured, and a generation time (or doubling time) was calculated based on the count. In the control group (Con), the generation time was averaged 46 hours and was highest as average 30 hours at a concentration of 10 ng/ml (see FIG. 8). In addition, the inhibitory effect on cancer cells was observed, and the generation time was observed after culturing a human-derived lung cancer cell line A549, and then an average generation time of the control group Con was 20 hours, whereas in the case of using long/ml of CKS, it could be seen that the average generation time was increased to average 25 hours. The average generation time was increased even at other concentrations, but the highest generation time was shown at 10 ng/ml (see FIG. 9).

Example 6

The human wisdom tooth was pulled to extract stem cells. While the stem cells were cultured, the content analysis for β-galactosidase was performed by adding long/ml of CKS. The suppression of the expression of β-galactosidase in the cells means extending the lifespan of the cell. The content analysis for β-galactosidase using mesenchymal stem cells, human tooth-derived stem cells, was performed by ELISA which was an enzyme immunity measuring method. As a result, in the case of treating CKS, the content of β-galactosidase was reduced in all of three persons in wisdom tooth-derived mesenchymal stem cells (Dental MSCs) isolated from three persons. That is, in a first subject Den1, the content of β-galactosidase was reduced by 16%, in a second subject Den2, the content of β-galactosidase was reduced by 10%, and in a third subject Den3, the content of β-galactosidase was reduced by 12%, as compared with the control group Con. The content of β-galactosidase of average 12.7% was reduced, which was related with the lifespan extension of the cells.

The present invention has industrial applicability to provide a pharmaceutical composition which contains ginseng saponin as an active ingredient by preparing the ginseng saponin as an active ingredient by removing a sugar attached to the active ingredient to be useful to increase the number of red blood cells and reduce triglycerides and to provide a pharmaceutical composition which contains ginseng saponin as an active ingredient which overcomes the problem on persistence of harmful organic solvents to be useful to increase the number of red blood cells, reduce triglycerides, differentiate the stem cells, and extend the lifespan of the cell.

The invention claimed is:
1. A composition containing ginseng saponin as an active ingredient which is useful for extending the lifespan of cells and promoting differentiation of cells, wherein the ginseng saponin is prepared by:
    exposing the ginseng to steam under a pressure of 1.1 kg/cm$^2$ while removing moisture at 121° C. for 10 minutes using an automatic temperature and humidity control device with a porous shelf (step S1);
    continuously injecting air into the ginseng subjected to the step S1 and cooling the ginseng to 90° C. or lower (step S2);
    repeating the steps S1 and S2 two times (step S3);
    cooling the ginseng to room temperature in an automatic temperature control device and pulverizing the ginseng to a particle size of 1 mm or less, after step S3 (step S4);
    extracting the saponin by adding 80% ethyl alcohol to the ginseng subjected to the step S4, and concentrating the extracted saponin (step S5);
    preparing a suspension by dissolving the concentrated saponin in ethanol and adding sterilized water, after step S5 (step S6);
    adding the suspension to and reacting the suspension with a pectinase enzyme solution drop by drop, after step S6 (step S7);
    precipitating the solution subjected to the reaction of step S7 by centrifugation (step S8);
    dissolving the generated precipitate in ethyl alcohol (step S9);
    suspending the dissolved precipitate by adding sterilized physiological saline solution (step (10));
    filtering the suspended precipitate (step S11); and
    resuspending the precipitate in sterile physiological saline solution (step S12).
2. The composition of claim 1, wherein when the composition is used in a method to extend the lifespan of the cells, the life span extension is suppressed when the cells are contacted by an effective amount of β-galactosidase.
3. The composition of claim 1, wherein the promoting of the differentiation of cells is promoting of differentiation of stem cells.

4. A composition containing ginseng saponin as an active ingredient which is useful for reducing triglycerides and increasing the number of red blood cells, wherein the ginseng saponin is prepared by, exposing the ginseng to steam under a pressure of 1.1 kg/cm$^2$ while removing moisture at 121° C. for 10 minutes using an automatic temperature and humidity control device with a porous shelf (step S1);

continuously injecting air into the ginseng subjected to the step S1 and cooling the ginseng to 90° C. or lower (step S2);

repeating the steps S1 and S2 two times (step S3);

cooling the ginseng to room temperature in an automatic temperature control device and pulverizing the ginseng to a particle size of 1 mm or less, after step S3 (step S4);

extracting the saponin by adding 80% ethyl alcohol to the ginseng subjected to the step S4, and concentrating the extracted saponin (step S5);

preparing a suspension by dissolving the concentrated saponin in ethanol and adding sterilized water, after step S5 (step S6);

adding the suspension to and reacting the suspension with a pectinase enzyme solution drop by drop, after step S6 (step S7);

precipitating the solution subjected to the reaction of step S7 by centrifugation (step S8);

dissolving the generated precipitate in ethyl alcohol (step S9);

suspending the dissolved precipitate by adding sterilized physiological saline solution (step (10);

filtering the suspended precipitate (step S11); and resuspending the precipitate in sterile physiological saline solution (step S12).

5. The composition of claim 1, wherein the ginseng saponin contains 90% or higher of protopanaxadiol-based saponin.

6. The composition of claim 5, wherein the protopanaxadiol-based saponin includes the compounds K, Rd, F2, and Rg3 which are active protopanaxadiols.

7. The composition of claim 4, wherein the ginseng saponin contains 90% or higher of protopanaxadiol-based saponin.

* * * * *